United States Patent
Douglas et al.

(10) Patent No.: US 11,124,754 B2
(45) Date of Patent: Sep. 21, 2021

(54) PRESSURE-CONTROLLED APPARATUS FOR OPTIMAL CELLULAR GROWTH

(71) Applicant: Nextern, Inc., White Bear Lake, MN (US)

(72) Inventors: Ryan Douglas, Stillwater, MN (US); Richard Farrell, Delwood, MN (US); David Bontrager, Minneapolis, MN (US)

(73) Assignee: Nextern, Inc., White Bear Lake, MN (US)

( * ) Notice: Subject to any disclaimer, the term of this patent is extended or adjusted under 35 U.S.C. 154(b) by 431 days.

(21) Appl. No.: 15/993,472

(22) Filed: May 30, 2018

(65) Prior Publication Data

US 2019/0002816 A1 Jan. 3, 2019

Related U.S. Application Data

(60) Provisional application No. 62/512,554, filed on May 30, 2017.

(51) Int. Cl.
| | |
|---|---|
| *C12M 1/34* | (2006.01) |
| *C12M 1/04* | (2006.01) |
| *C12M 1/12* | (2006.01) |
| *C12M 3/06* | (2006.01) |

(52) U.S. Cl.
CPC ............ *C12M 41/40* (2013.01); *C12M 23/24* (2013.01); *C12M 1/04* (2013.01); *C12M 3/06* (2013.01); *C12M 25/14* (2013.01); *C12M 27/14* (2013.01)

(58) Field of Classification Search
CPC ...... C12M 23/14; C12M 23/26; C12M 29/06; C12M 23/24; C12M 41/40
See application file for complete search history.

(56) References Cited

U.S. PATENT DOCUMENTS

| | | | | |
|---|---|---|---|---|
| 6,420,187 | B1 * | 7/2002 | Gilmore | G01N 1/2226 422/523 |
| 8,603,805 | B2 * | 12/2013 | Goodwin | B01F 13/0255 435/296.1 |
| 2009/0130704 | A1 * | 5/2009 | Gyure | C12M 37/04 435/41 |
| 2013/0064738 | A1 * | 3/2013 | Berger | B01J 4/008 422/521 |
| 2013/0082410 | A1 * | 4/2013 | Goodwin | C12M 23/14 261/42 |
| 2014/0349385 | A1 * | 11/2014 | Erdenberger | B01F 7/162 435/302.1 |
| 2017/0349874 | A1 * | 12/2017 | Jaques | B01F 15/0085 |

* cited by examiner

*Primary Examiner* — Jonathan M Hurst
(74) *Attorney, Agent, or Firm* — Craige Thompson; Thompson Patent Law; Timothy D. Snowden

(57) ABSTRACT

Apparatus and associated methods relate to an optimizable cellular growth chamber, where growth conditions are optimized by adjusting gas pressures through a gas permeable membrane. In an illustrative example, an apparatus may provide a volume to contain growth medium and the cells under propagation, where the volume has limited but non-zero pneumatic communication with a pressure-controlled chamber via a gas-permeable membrane. Associated apparatus and methods are proposed to manage desired growth conditions via deliberate control of parameters, such as partial pressures, for example.

20 Claims, 4 Drawing Sheets

PRESSURE-CONTROLLED APPARATUS FOR OPTIMAL CELLULAR GROWTH

CROSS-REFERENCE TO RELATED APPLICATIONS

This application claims the benefit of U.S. Provisional Application Ser. No. 62/512,554 titled "Managed Chamber for Cell Expansion," filed by Douglas, et al. on May 30, 2017.

This application incorporates the entire contents of the foregoing application(s) herein by reference.

TECHNICAL FIELD

Various embodiments relate generally to an apparatus and the associated methods to manage cell expansion processes and control growth medium stability.

BACKGROUND

Cell expansion is the process of growing cell cultures. Expansion processes put live cells in conditions that are favorable to cell growth and multiplication in order to propagate a primary sample to higher cell count.

SUMMARY

Apparatus and associated methods relate to an optimizable cellular growth chamber, where growth conditions are optimized by adjusting gas pressures through a gas permeable membrane. In an illustrative example, an apparatus may provide a volume to contain growth medium and the cells under propagation, where the volume has limited but non-zero pneumatic communication with a pressure-controlled chamber via a gas-permeable membrane. Associated apparatus and methods are proposed to manage desired growth conditions via deliberate control of parameters, such as partial pressures, for example, of interest.

Cells may be grown on fixed surfaces or suspended in fluid. Cells on fixed surfaces may be grown on a monolayer substrate or a 3D scaffold. Suspended cells may be grown in a moving (e.g., stirred) or stationary fluid. In many expansion processes, a growth medium is provided that carries nutrients, hormones, pH buffering agents, and other compounds to promote the expansion process. Composition of the growth medium may be carefully monitored and adjusted to maintain favorable conditions as cell growth consumes and produces various compounds.

Various embodiments may provide one or more advantages. For example, some implementations may provide compact portable environments for handling and conveying biological cultures between clean room environments. Some examples permit tissues or other materials to be developed in an optimized growth chamber environment without restriction to a clean room or laboratory location. Such examples may improve efficiency and reduce cost, while increasing flexibility and mobility, which may be particularly valuable in time-sensitive applications (e.g., life saving medical scenarios such as transplants). Optimal growth conditions may be maintained in some implementations. Quick connections may be made via access port(s) that may, for example, permit rapid connection and communication of media in a chamber to another chamber or source of nutrients, for example. Permeable gas membranes may permit, for example, efficient control of partial pressures of gases within the chamber to control, for example, growth rates in the chamber, either in a fixed location or during transport between sterile environments.

In some exemplary embodiments, a growth chamber may use a primary fluid-retaining volume to hold cell growth medium that has been inoculated with a live cell culture. The inoculation may occur before or after the medium is transferred into the expansion chamber.

The details of various embodiments are set forth in the accompanying drawings and the description below. Other features and advantages will be apparent from the description and drawings, and from the claims.

BRIEF DESCRIPTION OF THE DRAWINGS

Like reference symbols in the various drawings indicate like elements.

DETAILED DESCRIPTION OF ILLUSTRATIVE EMBODIMENTS

Figure 1:
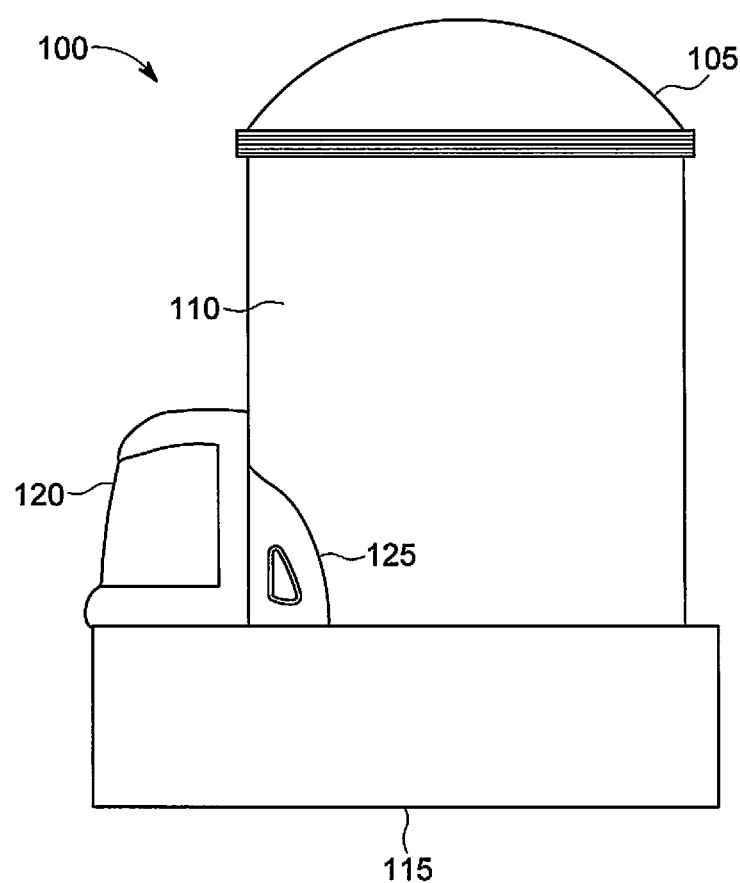
FIG. 1 depicts a planar front perspective view of an exemplary cell growth chamber.

FIG. 1 depicts a front perspective view of an exemplary cell growth chamber. A cell growth chamber [100] is constructed primarily of a growth chamber lid [105] and a growth chamber body [110]. A control element [115] functions as the floor of the growth chamber body [110]. The control element [115] may house various tubing, electronic elements, or sensors that allow for optimization of the growth conditions inside of the growth chamber body [110]. Exterior to the control element [115] and the growth chamber body [110] is a pump housing [120] to regulate gas pressures. Exterior to the control element [115] and interior to the growth chamber body [110] wall is a circulation mechanism [125] to aid in optimal exposure of any cellular matter to any elements that encourage growth. The depicted growth chamber [100] allows for volume-optimized cell growth using pressure differentials to introduce or eliminate gases through a gas permeable membrane. Within this document it is understood that the term "fluid" applies to matter in either liquid or gas state; therefore, if only gasses are being referred to or only liquids are being referred to, those terms will be used specifically.

Figure 2:
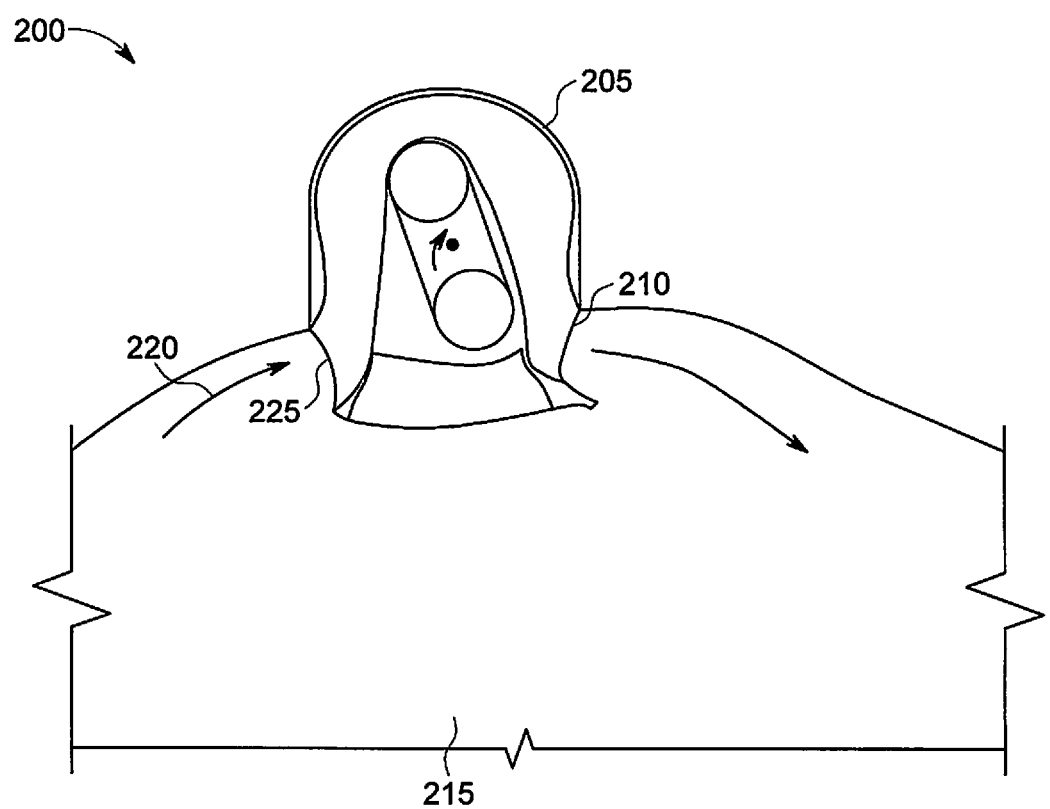
FIG. 2 depicts a cross-sectional view of an exemplary pump housing.

FIG. 2 depicts a cross-sectional view of an exemplary pump housing. The pump [200] is constructed of a peristaltic pump [205] with gaseous elements entering the pump mechanism through a gas entrance opening [210] and exiting the pump mechanism through a gas exit opening [225]. The gas circulates [220] into or removes gas from the growth chamber [215]. The peristaltic pump [205] configuration advantageously allows partial pressures to introduce or eliminate various gaseous elements in order to optimize the growth environment for the cellular material in the growth chamber [215].

Figure 3:
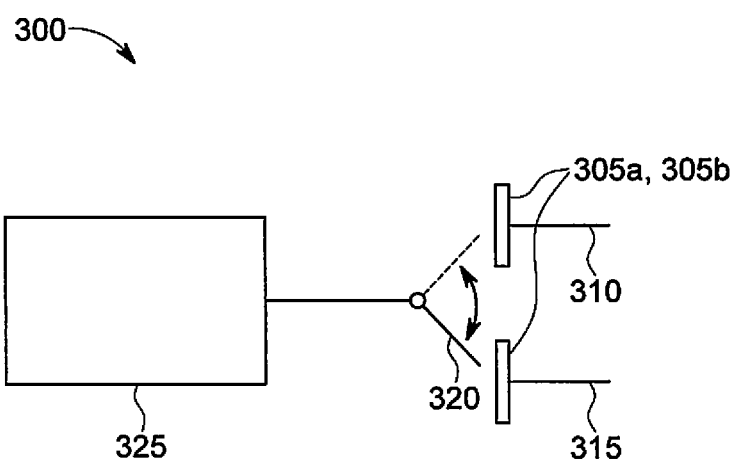
FIG. 3 depicts a diagrammatic view of an exemplary syringe pump configuration.

FIG. 3 depicts a diagrammatic view of an exemplary syringe pump configuration. The syringe pump configuration [300] may be constructed with at least one filtration mechanism [305a-b] access points, for access to various levels or to various elements within the growth chamber. An upper filtration mechanism [305a] may be a reservoir access port [310] and a lower filtration mechanism may be a growth chamber access port [315]. The syringe pump may access either port alternately by switching the direction of the syringe through the use of a directional mechanism [320] which then connects to the syringe pump [325]. The syringe pump advantageously may be used to introduce or eliminate materials, particularly non-gaseous materials, to or from the growth chamber.

Figure 4:
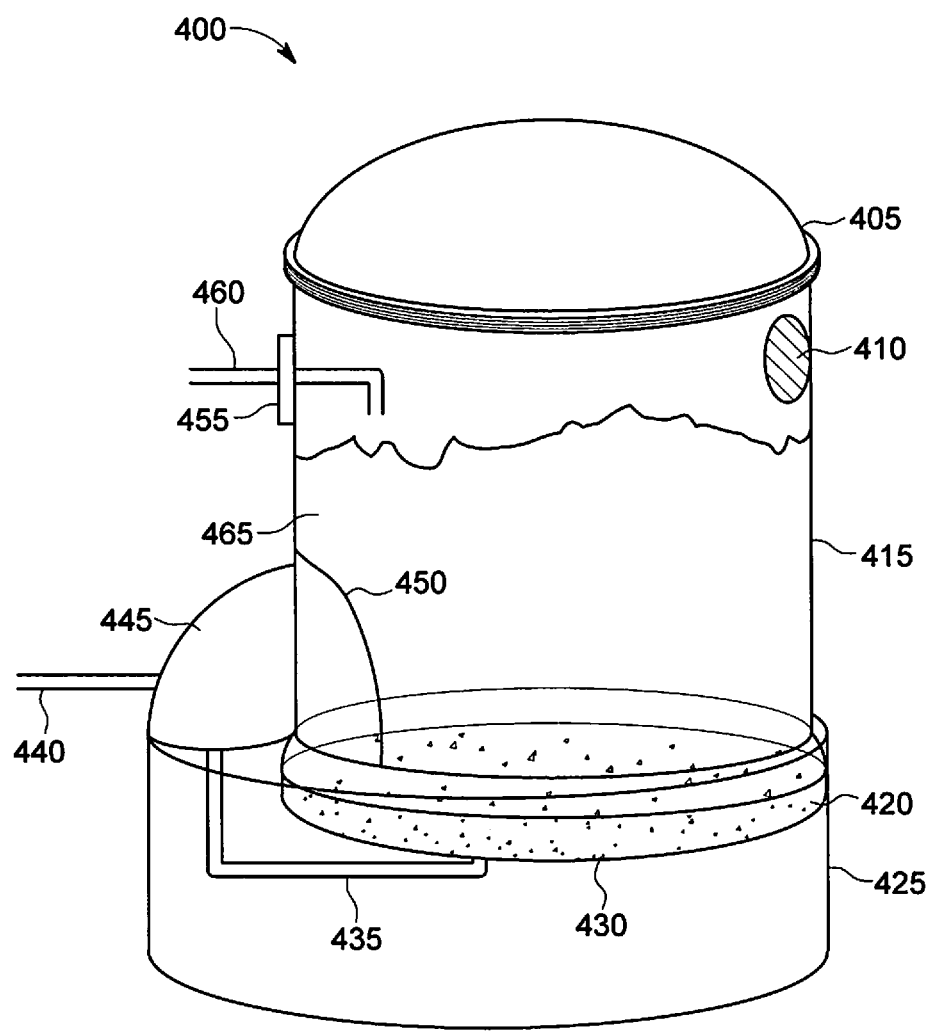
FIG. 4 front perspective view of an exemplary cell growth chamber with a gas introduction mechanism and an upper access port.

FIG. 4 front perspective view of an exemplary cell growth chamber with a gas introduction mechanism and an upper access port. A cell growth chamber [400] is primarily constructed of a growth chamber lid [405] and a growth chamber body [415]. To maintain an optimal cell growth environment, the cell growth chamber [400] is further constructed of a filtration mechanism [410]. The floor of the growth chamber body [415] at least partially is constructed of a gas permeable membrane [420], which allows gas communication between the growth chamber body [415] and the control housing [425]. The control housing may contain electronics, sensors, or tubing to monitor and optimize the growth chamber [400] environment. Additionally, the control housing contains a plenum [430] which receives gasses via inner gas tubing [435]. The plenum [430] provides a space for pressurized gas accumulation within the control housing [425] for the received gasses. The pump housing [445] receives gaseous elements from an external source via outer gas tubing [440] and expels these gaseous elements into the inner gas tubing [435]. These gaseous elements, once communicated into the growth chamber body [415] through the gas permeable membrane [420], are evenly distributed throughout the growth medium [465] using a circulation mechanism [450] that agitates the growth medium [465]. Non-gaseous materials are introduced or eliminated from the growth chamber [400] by accessing the interior of the growth chamber [400] by engaging at least one upper access port [455] via the upper access port tubing [460]. The upper access port construction advantageously allows for the introduction or elimination of non-gaseous elements allowing for further optimizing the growth environment within the growth chamber.

Although various embodiments have been described with reference to the Figures, other embodiments are possible. For example, the growth chamber may be open to atmosphere with no lid. For example, the growth chamber may not employ a circulation mechanism and may, instead, find it advantageous to allow the biological material to settle or separate into strata. The electronics and sensors within the control housing may, for example, consist of temperature or pressure control and monitoring elements. The growth chamber may need to be maintained at certain temperatures or pressures for optimal growth. In another example, the sensors may monitor or help control gaseous elements or pH of the growth medium. In an example, the filtration mechanism may be a standard HEPA filter.

In another example, an apparatus with a volume constructed to contain cell growth medium and cells under propagation may have one side of which is installed with a gas-permeable material that is non-permeable to liquids where that membrane also provides a pneumatic flow path between the growth volume and a second volume. The membrane separates the growth medium from an enclosed second volume to which a positive or negative pressure is applied. In this example, the apparatus may also have methods and apparatus for sensing and control that optionally: a) provide a controlled mixture of gases at a desired positive or negative pressure, where gases may be combined in situ or supplied as a premixed gas; b) measure composition, pressure, and/or volume of gas permeating the membrane; c) measure and control temperature of the growth medium within the internal volume; d) measure further parameters of interest of the growth medium, for example including pH, optical clarity/turbidity/absorption (intensity or spectral), dissolved oxygen, dissolved solids, and other direct measurements or proxy measurements that indicate the medium's suitability for cell expansion; e) selectively couple and decouple between the internal volume and a secondary reservoir volume containing additional growth medium to transfer medium between the internal growth volume and the secondary reservoir volume; or f) actuate a mechanism to circulate, stir, or otherwise cause continual or sporadic motion of the growth medium. Some of the above examples may combine all components into a single, integrated unit. Other examples may separate portions of the apparatus into two or more distinct pieces that may releasably interconnect.

In another example, the expansion chamber may be constructed of a fluid-retaining volume, at least one wall of which contains a membrane with a degree of permeability to gases. The chamber may also be constructed of an additional pressure-controlled, enclosed plenum volume that is separated from the fluid-retaining volume by the gas-permeable membrane. The plenum volume may be in fluid communication with an integral or otherwise connected pneumatic pumping system that can provide positive or negative pressure to the plenum volume. The "positive or negative pressure" may be measured in reference to external atmospheric pressure or the pressure within the fluid-retaining volume, if the fluid-retaining volume is enclosed.

Additionally, the plenum volume in the example embodiment may contain sensors as mentioned in paragraph 17 above. These sensors may be installed along a flow path within the system or in a third volume that is in fluid communication with the plenum volume. Sensors may be located in optimal locations for maintenance and protection from other elements. In various embodiments, plenum conditions may be set manually or automatically in response to measured conditions within the plenum and/or within the growth medium.

In another example, the volume's fluid-retaining enclosure may have a releasable lid or sidewall that when closed provides a fluid-impermeable seal. One or more sides of the chamber including the lid may be installed with an access port that may be closed, optionally providing a pressure-holding and fluid-impermeable seal, or opened to provide access to the interior of the chamber's growth volume. An access port may be used, for example, to extract samples, inject cells or other compounds to adjust composition of the growth medium, introduce additional sensors or actuators such as a stirring apparatus, transfer growth medium or other compounds into or out of the volume, and other processes that involve physical communication with the interior of the growth volume.

In another example, the growth chamber may have various gas permeable membranes installed on a plurality of sides of the internal volume, and each membrane may lead to its own non-shared plenum or a plurality of plenums that are shared among some or all of the membranes. In another example, the growth chamber may mate with an external centrifuge to allow mechanical separation of cells from the growth medium without transferring medium to a secondary vessel.

In another example, a particular method may be employed to control conditions of interest within the plenum volume. The purpose of the plenum volume is to optimally drive permeation of gas through the gas-permeable membrane from the growth medium into the plenum volume. In this example, one step applies negative pressure to the plenum volume by evacuating gas from the plenum volume with a pneumatic pump. Then, the decreased plenum pressure would drive higher permeation rate of gases out of the growth medium and through the membrane. After that, sensors within the plenum volume are used to measure the rate at which specific gases e.g. carbon dioxide or oxygen exit the growth medium, advantageously changing these gas's concentrations within the growth medium. Additional sensors monitoring the growth medium's properties may also be incorporated into a control algorithm. This algorithm may be deployed in various ways, for example, by use of a computer processor.

In an example, an external gas supply may provide gaseous material from a controlled source such as storage tanks containing one or more pure or mixed gases. Gases may be mixed to the desired proportions inside the plenum or by an external apparatus. In an example, a plenum may be in fluid communication with the top of the growth chamber. The plenum may provide an additional sensing and control area for gas to control gas pressure, composition, relative humidity, or temperature of a gas layer that may rest on top of the growth medium inside the growth chamber.

In another example, the growth chamber may be constructed with high granularity filters such as HEPA filters on any gas passage the system contains. Any plenum may have one or more external gas connections, or zero external gas connections and be fully contained. Embodiments may provide fluid-impermeable seals between the growth chamber and the ambient atmosphere, be open to atmosphere, or be separated by e.g. a HEPA filter at the top of the chamber.

In another example, a sensing and control element for the growth medium may be combined with the plenum sensing and control element. This example may be enabled to provide feedback to a user when human intervention is required and/or when adjustments to the system state to keep system parameters within acceptable limits is required or to bring the growth medium back within acceptable parameters is required.

In another example, the growth chamber may use a pump, which may be a peristaltic pump, to agitate and displace the growth medium, wherein the shape of the chamber and the shape, location, and orientation of the entry/exit orifices within the chamber create a circulating flow within the chamber. In any embodiment, entry/exit orifices may be located preferentially within the chamber near the top, bottom, or elsewhere in between. Embodiments may have orifices at one or more heights within the chamber to preferentially act on different compositions of the medium that settle to different levels in the chamber due to differences in specific gravity.

In another example, the growth chamber may be additionally constructed with a stirring apparatus in the growth medium actuated by rotation of an axle with an electric, pneumatic, or hydraulic drive. The stirring apparatus may be constructed of one or more members that effect movement of the growth medium when the axle is rotated. One or more members of the stirring apparatus may have integral temperature control elements to manage growth medium temperature. In an example, the stirring apparatus may use resistive or inductive heating elements, peltier-type cooling, or an enclosed fluid flow path to carry a temperature-controlled fluid that may be of a higher, lower, or equivalent temperature relative to the growth medium to respectively increase, decrease, or encourage stability of the medium's temperature.

Other embodiments may integrate temperature control elements into the side walls or base of the chamber; couple the temperature control elements to a passage the exits and re-enters the growth chamber where the growth medium is moved through the passage by a pumping mechanism, e.g. a peristaltic pump; or provide a temperature control element as an additional component that may be either placed at some fixed location within the growth chamber or placed freely within the medium and controlled via wireless or wired communication.

Other embodiments may place a magnetically permeable object within the growth medium. The object may rest at the bottom, float at the top, or suspend at some level within the medium. A magnet outside the growth chamber may be rotatable to effect rotation of the magnetically permeable object, inducing agitation or stirring of the medium. The magnetically permeable object might advantageously be inductively heated as a method of increasing growth medium temperature. Various embodiments may rotate the external driving magnet with an electric or fluid-driven motor, or by placing the magnet in a fluid's flow path wherein the geometries of the passage and the magnet and the fluid flow induce rotation of the driving magnet. Stirring mechanisms in any embodiment may be run continuously or non-continuously at one or more rotational speeds.

Other embodiments may include a reservoir volume containing additional growth medium. The system may transfer fluid between the reservoir volume and the growth chamber via selective activation of a pump or by opening and closing valves to allow or stop flow. Passage between the reservoir volume and the growth chamber comprises one or more distinct passages controlled by one or more actuators. One or more of the passages may allow fluid movement due to gravity as driven by the height of the growth chamber relative to the height of the reservoir. In another example the growth chamber may have two reservoirs—one for fluid that has not yet entered the growth chamber and one for fluid that has exited the growth chamber. The two reservoirs may be connected with an additional passage that optionally carries fluid through a number of processing steps to e.g. refresh growth medium nutrient content, add or remove hormones, adjust pH, separate cells or precipitate from the medium, measure properties e.g. optical absorption spectrum, or otherwise control or monitor properties of the fluid. Additional reservoirs may be provided to store compounds separately and mix at desired times or as intermediate fluid storage locations for the various processing steps. One or more of the reservoirs may be held at a higher or lower temperature than the growth chamber to advantageously enhance or attenuate chemical/biochemical reactions to drive assorted processing steps in a fluid or to encourage chemical and biological stability of a fluid. Growth medium control and processing may alternatively occur within passages in/out of the growth chamber and/or a reservoir.

The various examples may allow growth medium to be extracted, introduced, or refreshed to optimize conditions for the expansion process. One embodiment applies methods of monitoring cell growth status to optimally refresh the growth medium via biochemical processing and/or replacing old medium with new medium. When the system or the user monitors cell density and growth rate within the growth chamber via automated or manual extraction and automated or manual cell density measurement, expansion status can be determined and used to decide when to subculture the sample. To begin a subculture, various embodiments may: 1) separate cells to decant the spent growth medium before replacing with new medium; 2) use pump or gravity-feed methods to remove cell-bearing medium from the growth chamber for transfer to a separate chamber, to another reservoir within the system, or to a removable container for the purpose of e.g. cryogenic preservation; and 3) replace the removed cell-bearing medium with medium or fluids that bear no cells In another example, a growth chamber may start with an initial volume of growth medium that is less than the chamber's total internal volume. As the expansion progresses it may maintain optimal cell density by adding fluid more quickly than it removes fluid. Some embodiments may operate on the growth medium in a staged process, performing different steps during discrete steps of the expansion process. Other embodiments may enact continuous monitoring and respond to maintain specified conditions according to the current, measured state of the expansion process.

In another example, the growth chamber may be additionally constructed to support a passage between a single reservoir and the growth chamber. This embodiment places an orifice or set of orifices leading to one or more volumes capable of moving fluid with one or more pumps, by way of example a syringe pump. One or more of the orifices may optionally provide a filter element to prevent particulate exchange between the growth chamber volume and the reservoir volume. In this embodiment, the syringe pump may be actuated to withdraw medium from the growth chamber or the reservoir and to further inject the withdrawn medium into the growth chamber or the reservoir. Flow path in/out of the growth chamber/reservoir may be controlled with electromechanically-, pneumatically-, or hydraulically-actuated valves or passive spring valves or "flap valves" that use pressure differentials to operate.

Examples with both stirring mechanism and a transfer pump may actuate the two components with distinct actuators. Embodiments may alternatively actuate both components from the same power source, e.g. effect rotation in both with hydraulically driven motors that receive hydraulic power from one or more central actuators. Some embodiments may include further pumps and rotational actuators to transfer fluids among a plurality of passages and/or reservoirs. Those pumps and rotational actuators may similarly be driven by shared or distinct actuators or energy sources.

Some aspects of embodiments may be implemented as a computer system. For example, various implementations may include digital and/or analog circuitry, computer hardware, firmware, software, or combinations thereof. Apparatus elements can be implemented in a computer program product tangibly embodied in an information carrier, e.g., in a machine-readable storage device, for execution by a programmable processor; and methods can be performed by a programmable processor executing a program of instructions to perform functions of various embodiments by operating on input data and generating an output. Some embodiments may be implemented advantageously in one or more computer programs that are executable on a programmable system including at least one programmable processor coupled to receive data and instructions from, and to transmit data and instructions to, a data storage system, at least one input device, and/or at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example and not limitation, both general and special purpose microprocessors, which may include a single processor or one of multiple processors of any kind of computer. Generally, a processor will receive instructions and data from a read-only memory or a random-access memory or both. The essential elements of a computer are a processor for executing instructions and one or more memories for storing instructions and data. Storage devices suitable for tangibly embodying computer program instructions and data include all forms of non-volatile memory, including, by way of example, semiconductor memory devices, such as EPROM, EEPROM, and flash memory devices; magnetic disks, such as internal hard disks and removable disks; magneto-optical disks; and, CD-ROM and DVD-ROM disks. The processor and the memory can be supplemented by, or incorporated in, ASICs (application-specific integrated circuits). In some embodiments, the processor and the member can be supplemented by, or incorporated in hardware programmable devices, such as FPGAs, for example.

In some implementations, each system may be programmed with the same or similar information and/or initialized with substantially identical information stored in volatile and/or non-volatile memory. For example, one data interface may be configured to perform auto configuration, auto download, and/or auto update functions when coupled to an appropriate host device, such as a desktop computer or a server.

In some implementations, one or more user-interface features may be custom configured to perform specific functions. An exemplary embodiment may be implemented in a computer system that includes a graphical user interface and/or an Internet browser. To provide for interaction with a user, some implementations may be implemented on a computer having a display device, such as an LCD (liquid crystal display) monitor for displaying information to the user, a keyboard, and a pointing device, such as a mouse or a trackball by which the user can provide input to the computer.

In various implementations, the system may communicate using suitable communication methods, equipment, and techniques. For example, the system may communicate with compatible devices (e.g., devices capable of transferring data to and/or from the system) using point-to-point communication in which a message is transported directly from a source to a receiver over a dedicated physical link (e.g., fiber optic link, infrared link, ultrasonic link, point-to-point wiring, daisy-chain). The components of the system may exchange information by any form or medium of analog or digital data communication, including packet-based messages on a communication network. Examples of communication networks include, e.g., a LAN (local area network), a WAN (wide area network), MAN (metropolitan area network), wireless and/or optical networks, and the computers and networks forming the Internet. Other implementations may transport messages by broadcasting to all or substantially all devices that are coupled together by a communication network, for example, by using omni-directional radio frequency (RF) signals. Still other implementations may transport messages characterized by high directivity, such as RF signals transmitted using directional (i.e., narrow beam) antennas or infrared signals that may optionally be used with focusing optics. Still other implementations are possible using appropriate interfaces and protocols such as, by way of example and not intended to be limiting, USB 2.0, FireWire, ATA/IDE, RS-232, RS-422, RS-485, 802.11 a/b/g/n, Wi-Fi, WiFi-Direct, Li-Fi, BlueTooth, Ethernet, IrDA, FDDI (fiber distributed data interface), token-ring networks, or multiplexing techniques based on frequency, time, or code division. Some implementations may optionally incorporate features such as error checking and correction (ECC) for data integrity, or security measures, such as encryption (e.g., WEP) and password protection.

In various embodiments, a computer system may include non-transitory memory. The memory may be connected to the one or more processors may be configured for encoding data and computer readable instructions, including processor executable program instructions. The data and computer readable instructions may be accessible to the one or more processors. The processor executable program instructions, when executed by the one or more processors, may cause the one or more processors to perform various operations.

In various embodiments, the computer system may include Internet of Things (IoT) devices. IoT devices may include objects embedded with electronics, software, sensors, actuators, and network connectivity which enable these objects to collect and exchange data. IoT devices may be in-use with wired or wireless devices by sending data through an interface to another device. IoT devices may collect useful data and then autonomously flow the data between other devices.

A number of implementations have been described. Nevertheless, it will be understood that various modification may be made. For example, advantageous results may be achieved if the steps of the disclosed techniques were performed in a different sequence, or if components of the disclosed systems were combined in a different manner, or if the components were supplemented with other components. Accordingly, other implementations are contemplated within the scope of the following claims.

What is claimed is:

1. A pressure-controlled bio-growth chamber apparatus for optimal cellular growth comprising:
    an enclosure comprising:
        at least one outer wall defining an interior chamber with an opening, the outer wall being configured to receive a lid to cover the opening and releasably seal to the outer wall to seal the chamber from ambient atmosphere; and,
        a floor connected to the at least one wall to define a bottom boundary of the chamber;
    a control system housing exterior to and coupled to the enclosure;
    a pressure differential control mechanism operable to control a pressure differential with respect to the chamber; and,
    a circulation mechanism operably coupled to the enclosure and configured to agitate a liquid medium within the chamber,
    wherein the floor comprises a gas permeable membrane which is non-permeable to liquids, the membrane having a first side and a second side and adapted to communicate gaseous elements between an interior of said chamber and an exterior of said chamber while substantially containing the liquid medium in the chamber and on the first side of the gas permeable membrane,
    wherein said at least one outer wall and the gas permeable membrane define a plenum chamber between the second side of the gas permeable membrane and an exterior of said enclosure, the plenum chamber comprising at least one sensor disposed therein and operably coupled to the differential control mechanism,
    wherein the interior chamber is adapted to contain liquid media and biological matter supported substantially entirely by the gas permeable membrane on the first side thereof, and
    wherein the differential control mechanism is configured to: (1) controllably introduce at least one predetermined gaseous element into the plenum chamber through the membrane by applying a controlled negative partial pressure to the plenum, and (2) monitor, by the at least one sensor disposed in the plenum, at least one rate at which the at least one predetermined gaseous element exits the liquid medium in response to application of the negative partial pressure to the plenum.

2. The apparatus of claim 1, where said differential control mechanism comprises a pump.

3. The apparatus of claim 2, wherein the pump comprises a syringe pump in selective fluid communication with the plenum.

4. The apparatus of claim 2, wherein the pump is configured in selective fluid communication with the interior chamber.

5. The apparatus of claim 1, where the control system housing further encloses at least one additional sensor operably coupled to the differential control mechanism.

6. The apparatus of claim 1, where the control system housing further encloses temperature monitoring and control elements operably coupled to control the differential control mechanism in response to temperature measurements of contents in the interior chamber.

7. The apparatus of claim 1, where the control system housing further encloses pressure monitoring and control elements operably coupled to control the differential control mechanism in response to pressure measurements of contents in the interior chamber.

8. The apparatus of claim 1, where the control system housing further encloses pH monitoring and control elements operably coupled to control the differential control mechanism in response to pH measurements of contents in the interior chamber.

9. The apparatus of claim 1, further comprising at least one upper access mechanism allowing user-selective communication of non-gaseous elements between the interior of the enclosure and an exterior.

10. The apparatus of claim 1, where the lid is removably sealable to the enclosure.

11. A pressure-controlled bio-growth chamber apparatus for optimal cellular growth comprising:
    an enclosure comprising:
        at least one outer wall defining an interior chamber with an opening, the outer wall being configured to receive a lid to cover the opening and releasably seal to the outer wall to seal the chamber from ambient atmosphere; and,
        a floor connected to the at least one wall to define a bottom boundary of the chamber;
    a control system housing exterior to and coupled to the enclosure;
    a pressure differential control mechanism operable to control a pressure differential with respect to the chamber; and,
    a circulation mechanism operably coupled to the enclosure and configured to agitate a liquid medium within the chamber, wherein the floor comprises a gas permeable membrane having a first side and a second side and adapted to communicate gaseous elements between an interior of said chamber and an exterior of said chamber while substantially containing the liquid medium in the chamber and supported substantially by the first side of the gas permeable membrane, wherein said at least one outer wall and the gas permeable membrane define a plenum chamber between the second side of the gas permeable membrane and an exterior of said enclosure, and wherein the differential control mechanism is configured to (1) controllably introduce at least one predetermined gaseous element into the plenum chamber through the membrane by applying a controlled negative partial pressure to the plenum and (2) monitor, by at least one sensor disposed in the plenum, at least one rate at which the at least one predetermined gaseous element exits the liquid medium in response to application of the negative partial pressure to the plenum.

12. The apparatus of claim 11, where said differential control mechanism comprises a pump.

13. The apparatus of claim 12, wherein the pump comprises a syringe pump in selective fluid communication with the plenum chamber.

14. The apparatus of claim 12, wherein the pump is configured in selective fluid communication with the interior chamber.

15. The apparatus of claim 11, further comprising a sealable filtration mechanism.

16. The apparatus of claim 11, where the control system housing further encloses sensors operably coupled to the differential control mechanism.

17. The apparatus of claim 11, where the control system housing further encloses temperature monitoring and control elements operably coupled to control the differential control mechanism in response to temperature measurements of contents in the interior chamber.

18. The apparatus of claim 11, where the control system housing further encloses pressure monitoring and control elements operably coupled to control the differential control mechanism in response to pressure measurements of contents in the interior chamber.

19. The apparatus of claim 11, where the control system housing further encloses pH monitoring and control elements operably coupled to control the differential control mechanism in response to pH measurements of contents in the interior chamber.

20. The apparatus of claim 11, further comprising at least one upper access mechanism allowing user-selective communication of non-gaseous elements between the interior of the enclosure and an exterior.

* * * * *